US010806435B2

(12) United States Patent
Walther (10) Patent No.: US 10,806,435 B2
(45) Date of Patent: Oct. 20, 2020

(54) ENDOSCOPIC BIOPSY INSTRUMENT AND METHOD FOR TAKING A BIOPSY SAMPLE WITH HELICAL CUTTING EDGE PROVIDED AT THE TIP OF A GUIDEWIRE (71) Applicant: BibbInstruments AB, Lund (SE)

(72) Inventor: Charles Walther, Lund (SE)

(73) Assignee: BibbInstruments AB (SE)

( * ) Notice: Subject to any disclaimer, the term of this patent is extended or adjusted under 35 U.S.C. 154(b) by 929 days.

(21) Appl. No.: 14/419,383

(22) PCT Filed: Aug. 2, 2013

(86) PCT No.: PCT/EP2013/066275
§ 371 (c)(1),
(2) Date: Feb. 3, 2015

(87) PCT Pub. No.: WO2014/020150
PCT Pub. Date: Feb. 6, 2014

(65) Prior Publication Data
US 2015/0223788 A1    Aug. 13, 2015

(30) Foreign Application Priority Data

Aug. 3, 2012  (SE) .................................... 1250909

(51) Int. Cl.
*A61B 10/04*    (2006.01)
*A61B 1/005*    (2006.01)
(Continued)

(52) U.S. Cl.
CPC .............. *A61B 10/04* (2013.01); *A61B 1/005* (2013.01); *A61B 1/018* (2013.01); *A61B 1/2736* (2013.01);
(Continued)

(58) Field of Classification Search
None
See application file for complete search history.

(56) References Cited

U.S. PATENT DOCUMENTS 4,177,797 A   12/1979  Baylis et al.
4,919,146 A    4/1990  Rhinehart et al.
(Continued)

FOREIGN PATENT DOCUMENTS

EP    0 966 920    12/1999
EP    1 306 054     5/2003
(Continued)

OTHER PUBLICATIONS

International Search Report for PCT/EP2013/066275 dated Sep. 25, 2013.
(Continued)

*Primary Examiner* — Serkan Akar
(74) *Attorney, Agent, or Firm* — Condo Roccia Koptiw LLP (57) ABSTRACT An endoscopic biopsy instrument (1) is disclosed comprising a guide wire (2) arranged in a sheath (3), a drill device (5) arranged at a first end (4) of said guide wire (2), and an actuator (11) for actuating said drill device (5), said actuator being arranged at a second end (10) of said guide wire (2). The drill device (5) comprises an outer tube (6) and an inner cutting device (7). The inner cutting device (7) is slidable and rotatable inside said outer tube (6). The inner cutting device (7) has a helical cutting edge (8). An endoscope comprising such an endoscopic instrument (1) is also disclosed, as well as a method for taking a biopsy sample from a tissue of a subject.

11 Claims, 7 Drawing Sheets (51) Int. Cl.

| | | |
|---|---|---|
| *A61B 1/018* | (2006.01) | |
| *A61B 8/12* | (2006.01) | |
| *A61B 17/32* | (2006.01) | |
| *A61B 1/273* | (2006.01) | |
| *A61B 8/00* | (2006.01) | |
| *A61B 10/02* | (2006.01) | |
| *A61M 25/09* | (2006.01) | |
| *A61B 17/00* | (2006.01) | |

(52) U.S. Cl.
CPC ............... *A61B 8/12* (2013.01); *A61B 8/445* (2013.01); *A61B 10/0233* (2013.01); *A61B 17/32002* (2013.01); *A61M 25/09* (2013.01); *A61B 2010/0208* (2013.01); *A61B 2017/0034* (2013.01); *A61B 2017/00862* (2013.01); *A61M 2025/09183* (2013.01)

(56) References Cited

U.S. PATENT DOCUMENTS

| | | | |
|---|---|---|---|
| 5,146,928 A * | 9/1992 | Esser | A61B 10/04 600/569 |
| 5,423,799 A | 6/1995 | Shiu | |
| 5,507,296 A | 4/1996 | Bales et al. | |
| 5,591,202 A | 1/1997 | Slater et al. | |
| 5,666,965 A | 9/1997 | Bales et al. | |
| 5,707,392 A | 1/1998 | Kortenbach | |
| 5,810,826 A | 9/1998 | Akerfeldt et al. | |
| 5,865,724 A | 2/1999 | Palmer et al. | |
| 6,083,237 A | 7/2000 | Huitema et al. | |
| 6,743,185 B2 | 6/2004 | Weber et al. | |
| 2002/0138020 A1 | 9/2002 | Pflueger | |
| 2003/0114773 A1 | 6/2003 | Janssens | |
| 2005/0240147 A1* | 10/2005 | Makower | A61B 17/24 604/96.01 |
| 2006/0116605 A1* | 6/2006 | Nakao | A61B 10/0266 600/566 |
| 2008/0103412 A1 | 5/2008 | Chin | |
| 2008/0188767 A1* | 8/2008 | Oaki | A61B 1/018 600/566 |
| 2009/0118641 A1 | 5/2009 | Van Dam et al. | |
| 2012/0197157 A1 | 8/2012 | Ryan et al. | |

FOREIGN PATENT DOCUMENTS

| | | |
|---|---|---|
| EP | 1 849 414 | 10/2007 |
| WO | WO 2011/004776 | 1/2011 |
| WO | WO 2011/104692 | 9/2011 |

OTHER PUBLICATIONS

International Preliminary Report on Patentability for PCT/EP2013/066275 dated Sep. 30, 2014.
International Preliminary Report on Patentability for PCT/EP2013/066275 with Amended Sheets, dated Sep. 30, 2014.
Written Opinion of the International Searching Authority for PCT/EP2013/066275 dated Sep. 25, 2013.
"Rotex Screw Needle Biopsy Instrument®", Ursus Medical AB, 17 pages, Dec. 27, 2012.
Thorlacius et al., "Endoskopiskt Ultraljud Inom Gasteroenterologin", Lakartidningen, Non-English, 18 pages, Jan. 14, 2015.

* cited by examiner

ENDOSCOPIC BIOPSY INSTRUMENT AND METHOD FOR TAKING A BIOPSY SAMPLE WITH HELICAL CUTTING EDGE PROVIDED AT THE TIP OF A GUIDEWIRE

This application is the U.S. national phase of International Application No. PCT/EP2013/066275, filed 2 Aug. 2013, which designated the U.S. and claims priority to Swedish Patent Application No. 1250909-7, filed 3 Aug. 2012, the entire contents of each of which are hereby incorporated by reference.

TECHNICAL FIELD OF THE INVENTION

The present invention relates to an endoscopic biopsy instrument, to an endoscope comprising such an endoscopic biopsy instrument, as well as to a method for taking a biopsy sample from a tissue of a subject.

BACKGROUND ART

When evaluating various lesions and tumours, tissue samples may be acquired using a biopsy instrument. If a suspected lesion or tumour is located in or adjacent the gastrointestinal tract, an endoscopic biopsy instrument may be used. An example of an endoscopic biopsy instrument is described in U.S. Pat. No. 5,865,724. This endoscopic biopsy instrument is generally comprised of a forceps arranged at a distal end of two control wires, and a handle arranged at a proximal end of the control wires, the control wires being enclosed in a plastic sheath. When taking a tissue sample with this type of endoscopic biopsy instrument, the wires in their sheath are inserted in a working channel of an endoscope, and the forceps are advanced to the site in the gastrointestinal tract where the sample is to be taken. By operating the handle of the endoscopic biopsy instrument, the forceps may be manoeuvred to scoop out a sample from the surface of the tissue.

For some diagnostic purposes the millimetre-sized sample thus retrievable is sufficient. However, for some types of lesions and tumours, such a small and superficial sample is inadequate for making a diagnosis. This is the case, e.g., for submucosal tumours, such as gastrointestinal stromal tumours (GIST). Since these tumours are located beneath the mucosa of the stomach or intestines, the forceps of the above-mentioned type of endoscopic biopsy instrument cannot reach into the tumour and retrieve a sufficiently large sample. Therefore, in order to get a sample that makes it possible to diagnose a submucosal tumour, it is often necessary to retrieve the sample surgically. Unfortunately, the fact that a patient has had surgery for diagnostic purposes increases the risk of complications, and reduces the survival rate, even if a malignant tumour is removed during subsequent therapeutic surgery. Thus, a need for an improved endoscopic biopsy instrument, which makes it possible to take larger samples and/or samples at a larger depth, e.g., beneath the mucosa of the gastrointestinal tract, remains.

SUMMARY OF THE INVENTION

It is an object of the invention to provide an endoscopic biopsy instrument, which overcomes the problems described above.

It is also an object of the invention to provide an endoscope which overcomes these problems.

A further object of the invention is to provide a method for taking a biopsy sample from a tissue of a subject, which overcomes the problems described above.

According to a first aspect of the invention, these and other objects are achieved, in full or at least in part, by an endoscopic biopsy instrument comprising:
a guide wire arranged in a sheath,
a drill device arranged at a first end of said guide wire, and
an actuator for actuating said drill device, said actuator being arranged at a second end of said guide wire,
wherein said drill device comprises an outer tube and an inner cutting device, said inner cutting device being slidable and rotatable inside said outer tube, said inner cutting device having a helical cutting edge. With such an endoscopic biopsy instrument, it is possible to take a biopsy sample at a greater depth as compared to prior art instruments. Further, a larger sample may be taken. Especially for investigating submucosal tumours, it is important to be able to take the sample at a greater depth, since otherwise it may not be possible to reach the tumour, through the overlying tissue. For other types of tumours, it is useful to get a larger sample, since this may provide more diagnostic material.

The sheath may have a diameter of 1-5 mm in order to fit in a working channel of an endoscope. The diameter of the drill device may be adapted to the diameter of the sheath, and may be 0.5-4 mm, generally 1-2 mm.

In an embodiment, the outer tube is advancable over the inner cutting device on an outside of said inner cutting device. Thereby, the outer tube may be advanced over the inner cutting to enclose the sample cut out from the tissue.

The inner cutting device of the drill device may comprise an inner core, said helical cutting edge being formed on a helical flange surrounding said inner core. In this manner, a rigid inner cutting device may be achieved, which may penetrate even tough tissues, such as the mucosa of the gastrointestinal tract.

The inner cutting device may be made of metal. Metal is readily machinable to the desired helical shape and may readily be sharpened to present a cutting edge. Metal is particularly advantageous if the endoscopic biopsy instrument is used in an endoscope comprising an ultrasound probe, since metal is visible in an ultrasonogram. Thus, the operator may, in an image acquired by the ultrasound probe, for instance see how deep into the tissue the inner cutting device has penetrated.

In an embodiment, the outer tube of the drill device has a cutting front edge. In this manner, the sample may even more securely be cut out from the tissue, should it not be completely cut off by the helical cutting edge of the inner cutting device.

At the second end, the guide wire may comprise an outside thread, and the actuator may comprise a rotatable portion having an inside thread, the inside thread being engagable with the outside thread of the guide wire for advancing the guide wire inside said sheath. In this manner, an easily manoeuvrable guide wire advancing device may be achieved. In one embodiment, the operator may advance the guide wire by simply rotating the rotatable portion between his or her thumb and index finger.

Alternatively, at the second end, the guide wire may comprise a teethed portion, and the actuator may comprise a toothed gear, the toothed gear being engagable with the teethed portion of the guide wire for advancing the guide wire inside the sheath. This is another way of achieving an easily manoeuvrable guide wire advancing device. In one embodiment, the operator may advance the guide wire by simply rotating the toothed gear with his or her index finger.

The actuator may comprise a plunger arranged to advance said outer tube of said drill device on an outside of said inner cutting device. In this manner, an easily manoeuvrable outer tube advancing device may be achieved.

The actuator may comprise a second rotatable portion arranged to advance said outer tube of said drill device on an outside of said inner cutting device. This is another way of obtaining an easily manoeuvrable outer tube advancing device.

According to a second aspect of the invention, these and other objects are achieved, in full or at least in part, by an endoscope comprising:

an endoscopic insertion tube, an imaging device arranged in said endoscopic insertion tube, an endoscopic biopsy instrument of the invention arranged in said endoscopic insertion tube. With such an endoscope, the same advantages may be achieved as with the endoscopic biopsy instrument according to the first aspect of the invention. In the endoscope, the endoscopic biopsy instrument may be embodied in the same ways as the endoscopic biopsy instrument according to the first aspect of the invention, with the same advantages.

According to an embodiment, the imaging device is an ultrasound probe. Ultrasonic imaging is particularly advantageous for evaluating submucous tumours.

According to a third aspect of the invention, these and other objects are achieved, in full or at least in part, by a method for taking a biopsy sample from a tissue of a subject, comprising:

providing an endoscopic biopsy instrument comprising a guide wire arranged in a sheath, a drill device arranged at a first end of said guide wire, and an actuator for actuating said drill device, said actuator being arranged at a second end of said guide wire, wherein said drill device comprises an outer tube and an inner cutting device, said inner cutting device being slidable and rotatable inside said outer tube, said inner cutting device having a helical cutting edge, inserting said first end of said guide wire into a body cavity of said subject, advancing said guide wire until said drill device is applied to a surface of the tissue from which the biopsy sample is to be taken, advancing said guide wire inside said sheath such that said inner cutting device of said drill device is rotatingly bored into said tissue, such that the biopsy sample is cut out from said tissue, enclosing said biopsy sample in said outer tube by a translational movement of said outer tube in relation to said inner cutting device, and retrieving said biopsy sample by withdrawing said first end of said guide wire from said body cavity. With such a method, it is possible to take a biopsy sample from a greater depth as compared to prior art methods. It is also possible to take a larger sample.

The body cavity may be part of the gastrointestinal tract of the subject.

In a variant of the method, the outer tube is advanced over the inner cutting device on an outside of the inner cutting device. In this way, the sample cut out by the inner cutting device is enclosed by the outer tube.

The endoscopic biopsy instrument may be inserted in an endoscopic insertion tube of an endoscope, said endoscope comprising an imaging device arranged in said endoscopic insertion tube. In this way, the endoscopic biopsy instrument may be securely guided to the site where the biopsy sample is to be taken.

Generally, the method of the invention may be varied in accordance with the different embodiments of the first aspect of the invention, with the same accompanying advantages.

Other objectives, features and advantages of the present invention will appear from the following detailed disclosure, from the attached claims, as well as from the drawings. It is noted that the invention relates to all possible combinations of features.

Generally, all terms used in the claims are to be interpreted according to their ordinary meaning in the technical field, unless explicitly defined otherwise herein. All references to "a/an/the [element, device, component, means, step, etc.]" are to be interpreted openly as referring to at least one instance of said element, device, component, means, step, etc., unless explicitly stated otherwise. The steps of any method disclosed herein do not have to be performed in the exact order disclosed, unless explicitly stated.

As used herein, the term "comprising" and variations of that term are not intended to exclude other additives, components, integers or steps.

BRIEF DESCRIPTION OF THE DRAWINGS

The invention will be described in more detail with reference to the appended schematic drawings, which show an example of a presently preferred embodiment of the invention.

DETAILED DESCRIPTION OF PREFERRED EMBODIMENTS OF THE INVENTION

Figure 1:
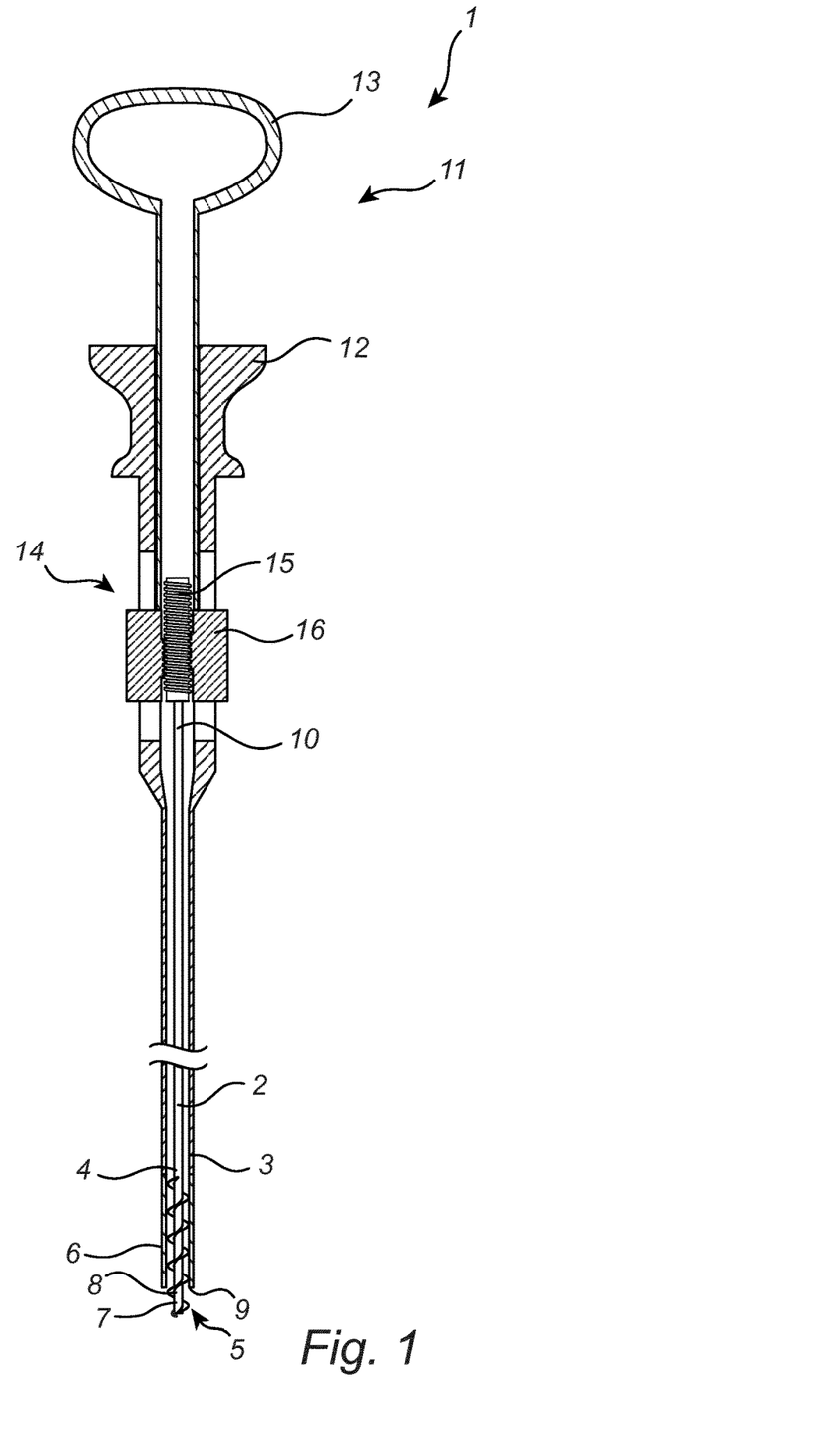
FIG. 1 is a cross sectional view of an endoscopic biopsy instrument according to an embodiment.

In FIG. 1, an endoscopic biopsy instrument 1 is shown. The endoscopic biopsy instrument 1 comprises a guide wire 2 arranged in a sheath 3. At a first, distal end 4 of the guide wire 2, a drill device 5 is arranged. The drill device 5 comprises an outer tube 6 and an inner cutting device 7. The inner cutting device 7 is slidable and rotatable inside the outer tube 6, and has a helical cutting edge 8. The outer tube 6 is cylindrical and has a straight edge 9.

At a second, proximal end 10 of the guide wire 2, an actuator 11 comprising a handle 12 and a plunger 13 is arranged. The actuator 11 further comprises a guide wire advancing device 14. The guide wire advancing device comprises a threaded portion 15 at the proximal end of the guide wire 2 having an outside thread, and a rotatable portion 16 or nut having an inside thread. The threaded portion 15 of the guide wire 2 is engagable with the nut 16, such that rotation of the nut 16 causes the guide wire to rotate and move in its longitudinal direction, thus moving along the inside of the sheath 3.

Figure 4:
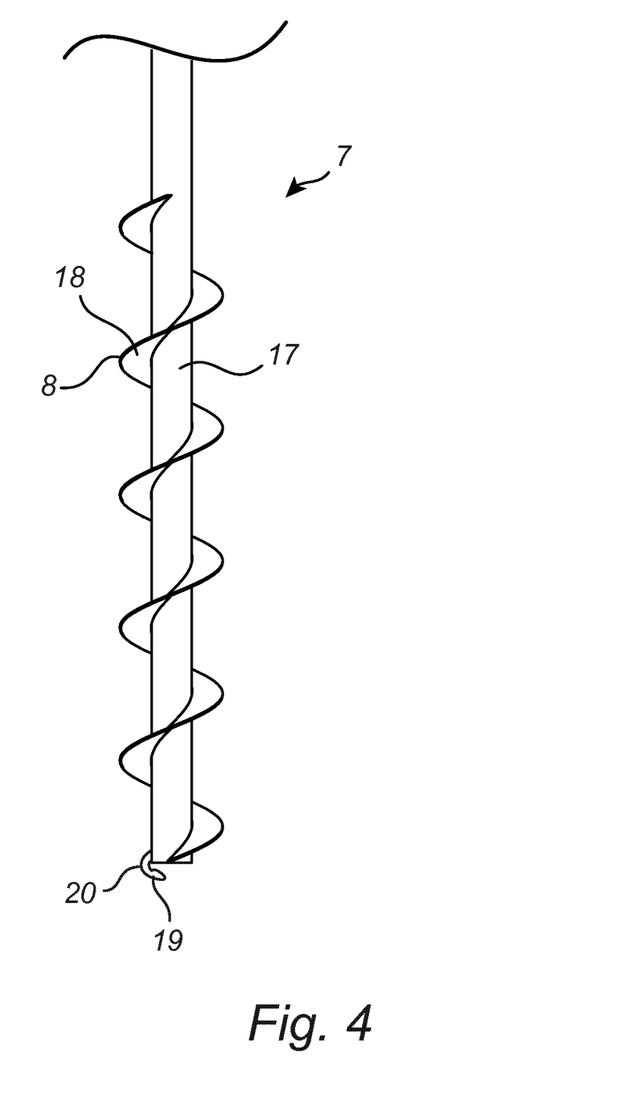
FIG. 4 is a detail view of an inner cutting device of the endoscopic biopsy instrument of FIG. 1 or FIG. 3.

As may be seen more clearly in FIG. 4, the inner cutting device 7 has an inner core 17 surrounded by a helical flange 18. The helical cutting edge 8 of the inner cutting device 7 is formed on the helical flange 18. The helical flange 18 forms more than one complete winding or turn around the inner core 17. At the distal end 19 of the inner cutting device 7 a hook or anchoring portion 20 is formed on the helical flange 18.

Figure 2:
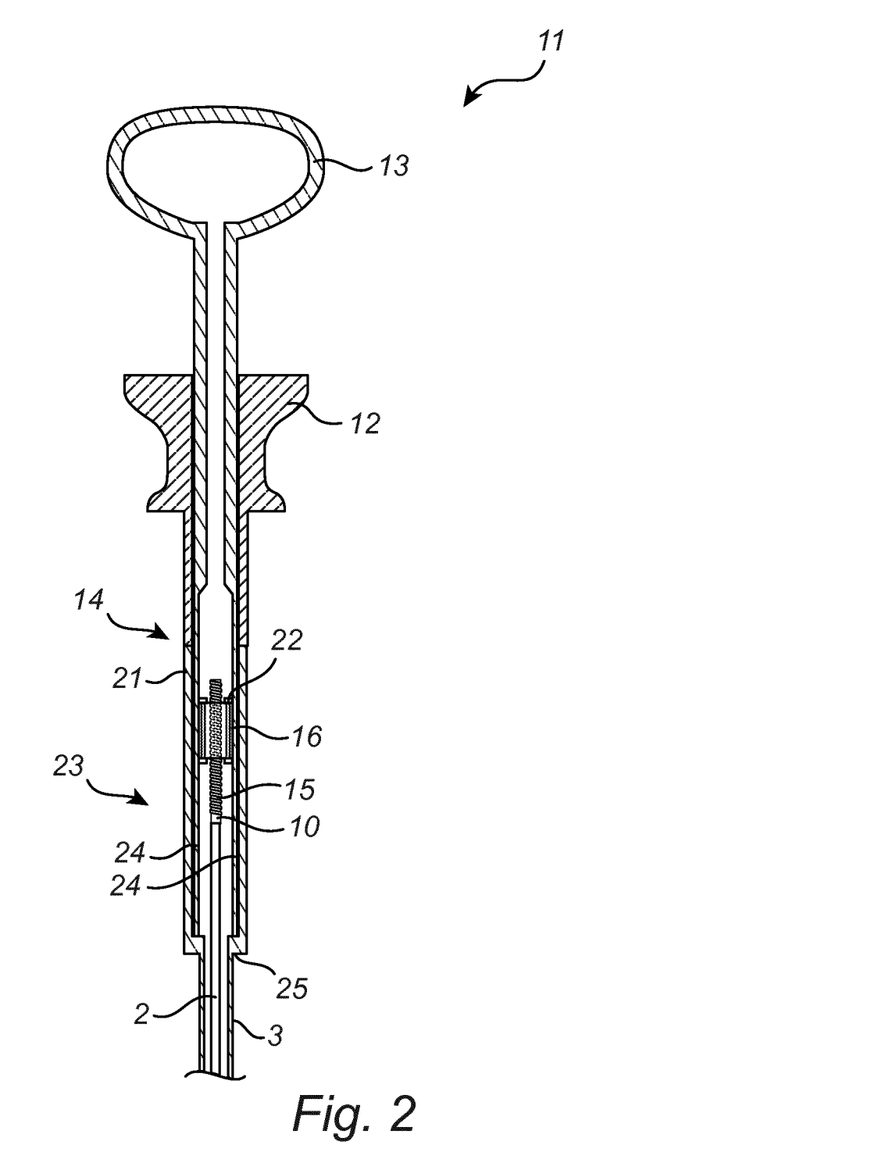
FIG. 2 is a detail view of an actuator of the endoscopic biopsy instrument of FIG. 1.

With reference to FIG. 2, the actuator 11 further comprises a housing 21 in which the wire, via the nut 16, is retained at retaining points 22, and a sheath advancing device 23 in the form of bars 24 attached to the plunger 13. Abutment portions 25 of the bars abut a cut-out edge of the sheath 3, such that when the plunger 13 is depressed, the bars 23, via the abutment portions 24, push the sheath 3 outwardly from the housing 21. Thereby, the sheath 3 advances the outer tube 6 of the drill device 5 over the inner cutting device 7 on an outside of the inner cutting device 5.

Figure 3:
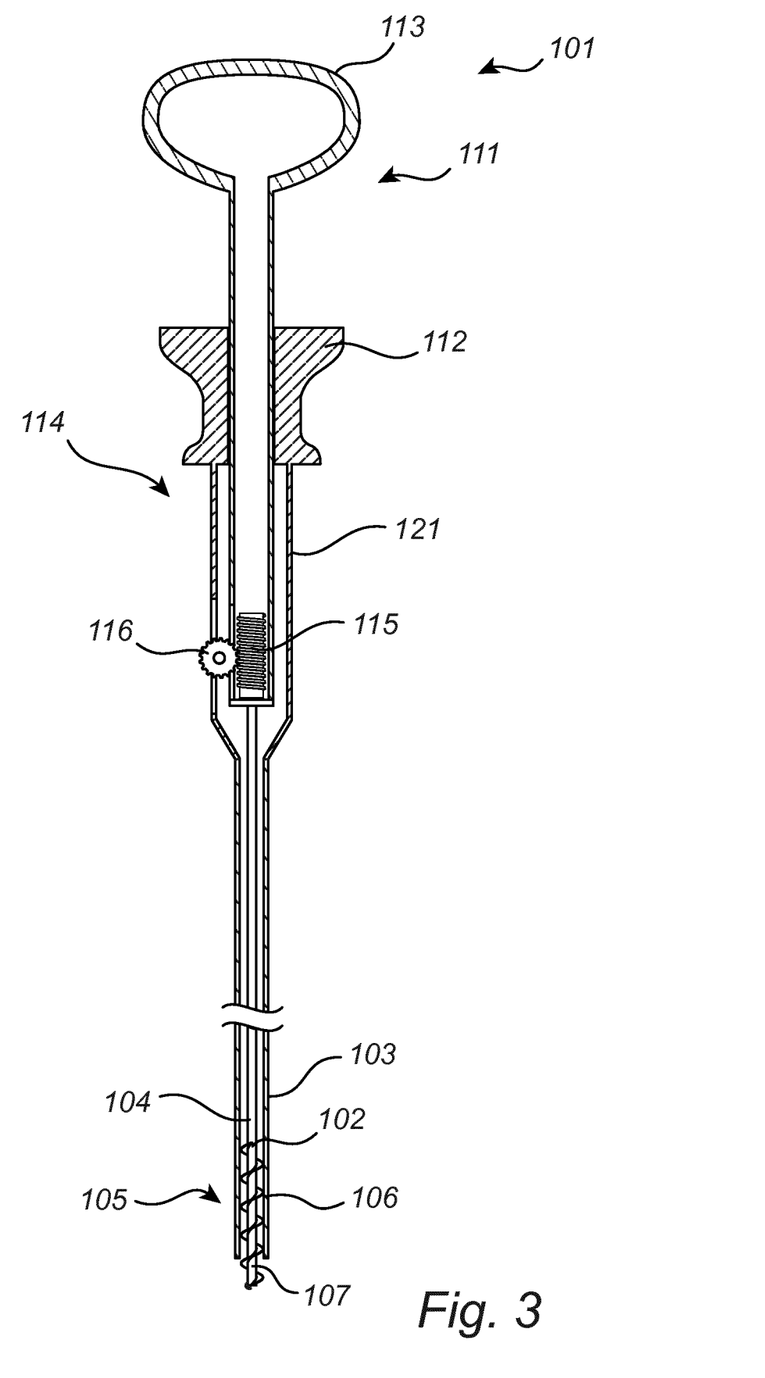
FIG. 3 is a cross sectional view of an endoscopic biopsy instrument according to a second embodiment.

In FIG. 3, an endoscopic biopsy instrument 101 according to a second embodiment is shown. Except for the actuator 111, the endoscopic biopsy instrument 101 in FIG. 3 has the same structure as the endoscopic biopsy instrument in FIG. 1. Like parts are in the embodiment in FIG. 3 marked with the same reference numerals as used in FIG. 1, but with the addition of 100 on each reference numeral.

Thus, the endoscopic biopsy instrument 101 comprises a guide wire 102 arranged in a sheath 103. At a distal end 104 of the guide wire 102 a drill device 105 of the same construction as the drill device 5 shown in FIG. 1 is arranged. The inner cutting device 107 is of the same construction as that shown in detail in FIG. 4. At the proximal end 110 of the guide wire 102, an actuator 111 is arranged. The actuator 111 comprises a handle 112, a plunger 113, and a guide wire advancing device 114. Different from the embodiment shown in FIGS. 1 and 2, the guide wire advancing device 114 comprises a teethed portion 115 at the proximal end of the guide wire 102, and a toothed gear 116, which is engagable with the teethed portion 115 of the guide wire 102. By rotating the toothed gear 116, the guide wire 102 may be rotated and advanced in its longitudinal direction, thus moving along the inside of the sheath 103.

Figure 6:
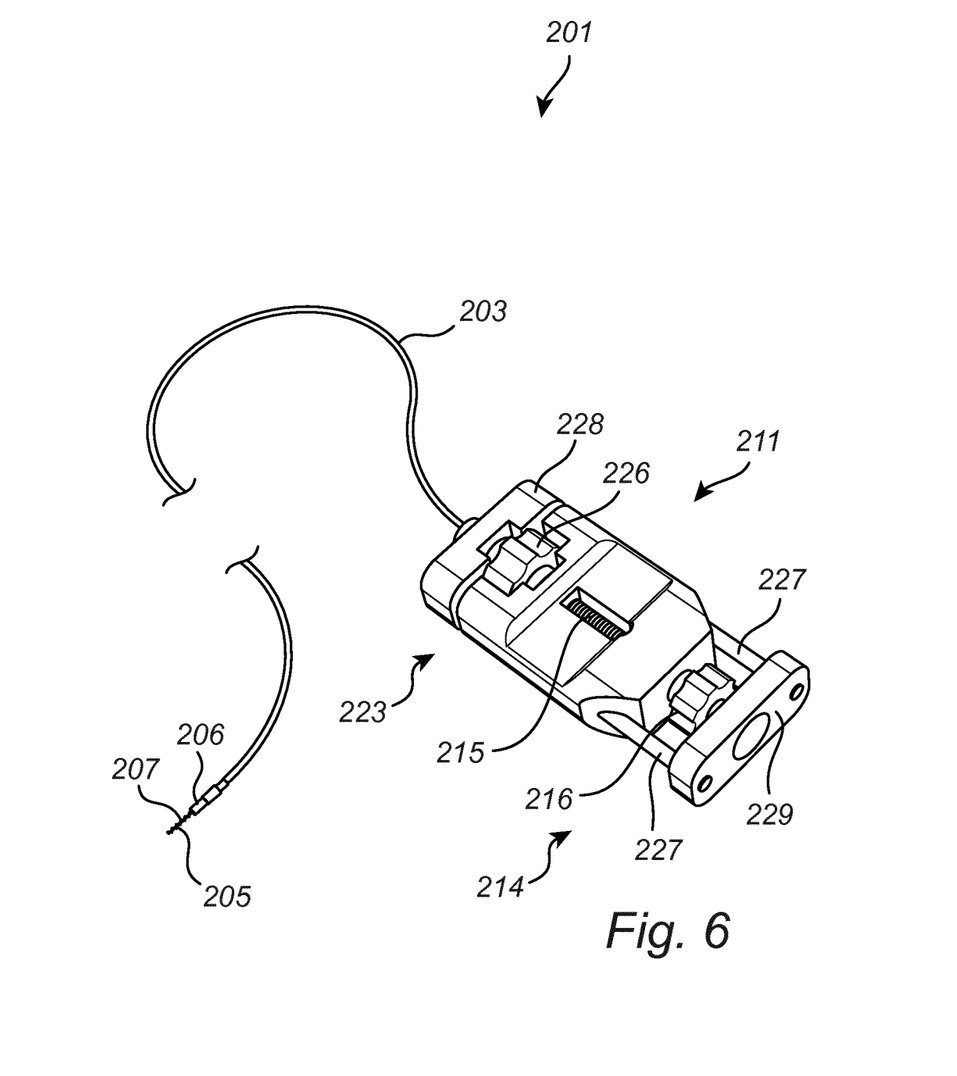
FIG. 6 is a detail view of an actuator of an endoscopic biopsy instrument according to a third embodiment in a first position.

In FIG. 6, an endoscopic biopsy instrument 201 according to a third embodiment is shown. Except for the actuator 211, the endoscopic biopsy instrument 201 in FIG. 6 has the same structure as the endoscopic biopsy instrument in FIG. 1. Like parts are in the embodiment in FIG. 6 marked with the same reference numerals as used in FIG. 1, but with the addition of 200 on each reference numeral.

Figure 7:
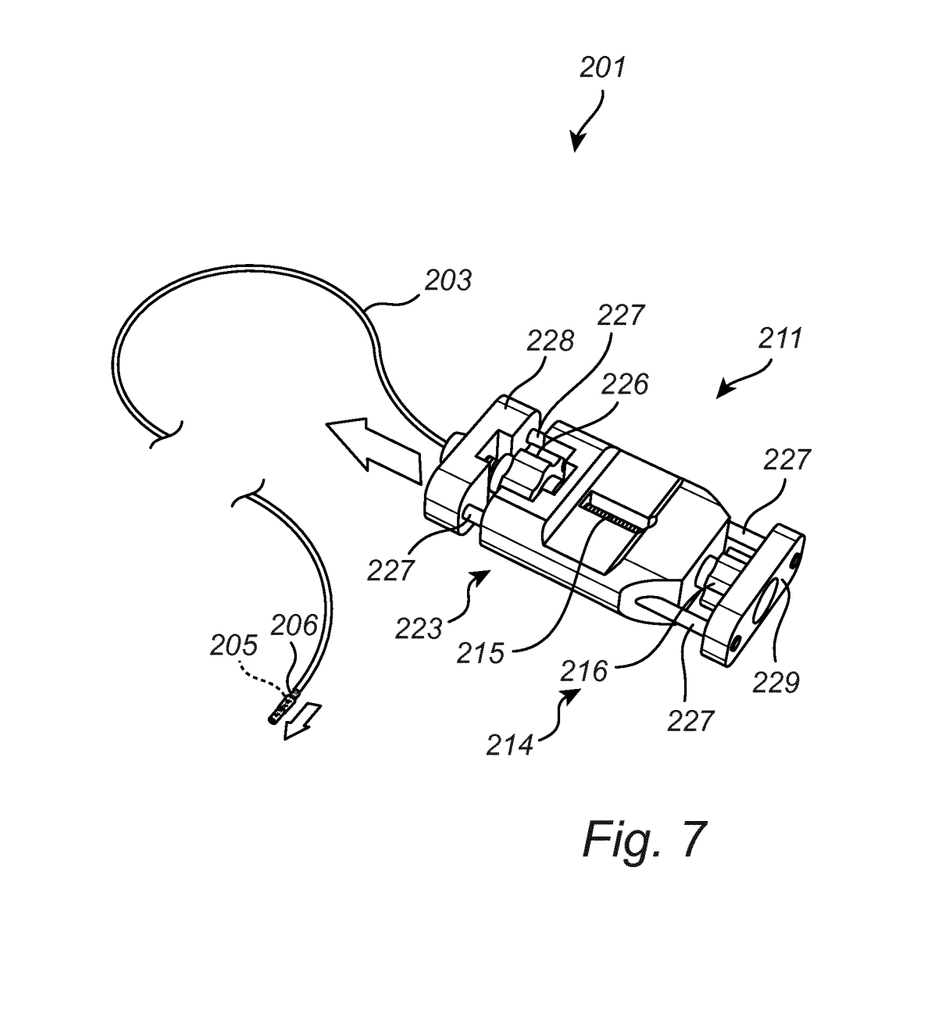
FIG. 7 is a detail view of the actuator of FIG. 6 in a second position.

The actuator 211 comprises a guide wire advancing device 214 which similarly to the embodiment shown in FIG. 1 comprises a threaded portion 215 at the proximal end of the guide wire having an outside thread, and a first rotatable portion 216 or nut having an inside thread. The threaded portion 215 of the guide wire is engagable with the wheel or nut 216, such that rotation of the nut 216 causes the guide wire to rotate and move in its longitudinal direction, thus moving along the inside of the sheath 203. The outer tube advancing device 223 differs from the one in the first embodiment in that it comprises a second rotatable portion in the form of a second wheel or nut 226. Rotation of the second nut 226 causes a sheath advancing portion 228 connected to two parallel guide bars 227 to travel in a distal direction from a position shown in FIG. 6 to a position shown in FIG. 7, thereby advancing the sheath 203. The sheath 203 in turn advances the outer tube 206 of the drill device 205 over the inner cutting device on an outside of the inner cutting device. In the embodiment shown, the outer tube advancing device 223 additionally comprises an end block 229 attached to the proximal end of the guide bars 227. As an alternative to rotating the second nut 226, the end block 229 may be depressed, thereby advancing the sheath advancing portion 228, which in turn advances the sheath 203, and thereby the outer tube 206.

In all of the shown embodiments, the sheath is made of a medical grade plastic material, whereas the outer tube and inner cutting device of the drill device are made of medical grade metal.

Figure 5:
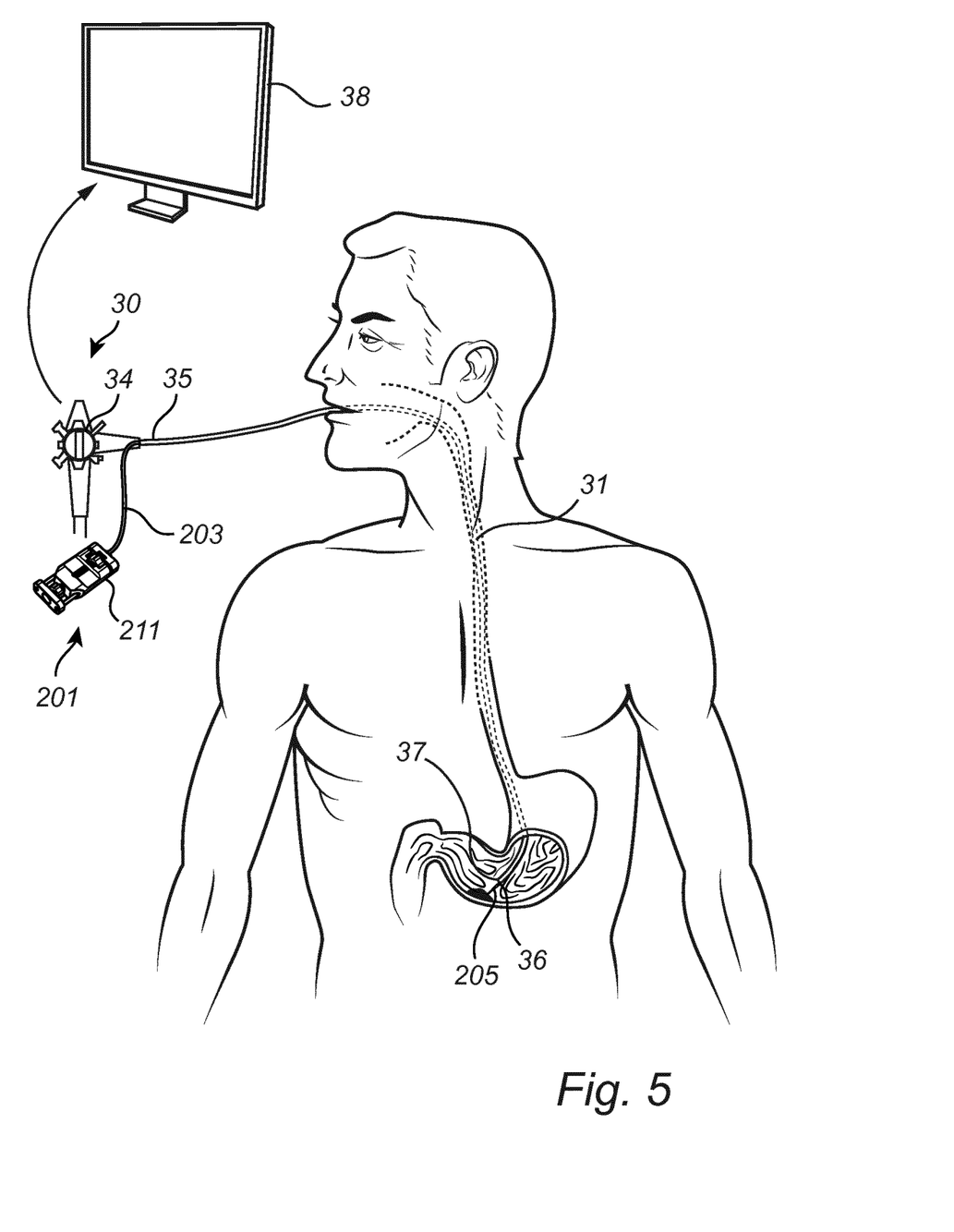
FIG. 5 is a cross sectional view showing use of an endoscope according to an embodiment.

An endoscopic biopsy instrument according to either embodiment may be inserted in an endoscope 30 and used in the way schematically illustrated in FIG. 5. An example of an endoscope with which the endoscopic biopsy instrument of the invention may be used may be seen in EP-1 849 414. In the following description of FIG. 5, the reference numerals used for the embodiment shown in FIG. 6 are used, but the endoscopic biopsy instrument according to the embodiment shown in FIG. 1 or FIG. 3 may just as well be used in the same way.

The endoscopic biopsy instrument 201 is inserted in a working channel of an endoscopic insertion tube 31 of the endoscope 30. A control unit 34 for the endoscope 30 is arranged at a proximal end 35 of the endoscopic insertion tube 31. At a distal end 36 of the insertion tube 31, an imaging device in the form of an ultrasound probe 37 or camera is arranged. Images captured by the ultrasound probe 37 or camera may be displayed on a display 38.

In the illustration in FIG. 5, the endoscope is a gastroscope 30, which is inserted through the mouth of a patient. The insertion tube 31 is advanced trough the oesophagus, down into the stomach, until the distal end 36 of the insertion tube 31 reaches the site which is to be investigated. Using the images acquired by the ultrasound probe 37 or camera, the operator may see the investigated site on the display 38. Since the inner cutting device 207 is made of metal, it is visible in an ultrasonogram. During insertion of the endoscopic insertion tube 31 to the site to be investigated, the inner cutting device 207 is enclosed in the outer tube 206, such that the inner cutting device 207 does not injure the mucosa along the passage through the mouth, oesophagus and stomach, and such that the sample taken is not soiled by tissue accidentally caught by the inner cutting device 207 before the site to be investigated is reached. When the desired location is reached, the distal end 19 of the inner cutting device 207 of the endoscopic biopsy instrument 201 is applied to the surface of the mucosa, and the hook 20 is anchored in the mucosa. By rotating the first nut 216, the operator advances the inner cutting device 207, boring it into and through the mucosa, and into the lesion or tumour to be evaluated. The inner cutting device 207 may be rotated a plurality of turns, in order to get a large sample from the quite tough mucous tissue.

With a sufficiently long inner cutting device 207, the inner cutting device 207 may also be bored through the lesion or tumour, thereby also including some overlying tissue in the sample. In this manner, a layered sample may be obtained, thereby enabling orientation of the retrieved biopsy sample. Once the inner cutting device 207 has been bored into the lesion or tumour to a depth which the operator, guided by the images acquired by the ultrasound probe 37, considers is sufficient, the operator rotates the second nut 226, thereby advancing the outer tube 206 of the drill device 205 on the outside of the inner cutting device 207. In this manner, the sample cut out and caught on the flange 18 of the inner cutting device 207 is enclosed by the outer tube 206. Subsequently, the endoscopic biopsy instrument is withdrawn from the endoscope. Once the drill device 205 is outside the body of the patient, the outer tube 206 of the drill device 205 may be retracted, exposing the sample on the flange 18 of the inner cutting device 207. The sample is removed from the inner cutting device 207 and prepared for microscopic examination. Generally, more than one sample will be taken by reinserting the endoscopic biopsy instrument 201 in the endoscope 30, boring the inner cutting device 207 into the tissue, enclosing the cut-out sample in the outer tube 206, and withdrawing the endoscopic biopsy instrument 201 from the endoscope 30. This procedure may be repeated a number of times, until a desired number of biopsy samples have been obtained. When the desired number of samples has been retrieved, the endoscope may be withdrawn from the stomach, out through the oesophagus and mouth.

The skilled person realises that a number of modifications of the embodiments described herein are possible without departing from the scope of the invention, which is defined in the appended claims.

For instance, although the endoscope shown in FIG. 5 is a gastroscope, the invention is equally applicable to other endoscopes, such as coloscopes, and bronchoscopes.

The imaging device may be a camera. For investigating many types of tumours, a camera will be the first choice of imaging device. However, for investigating submucous tumours, the use of an ultrasound probe has been shown to give better results (See, e.g., Thorlacius et al. Endoskopiskt ultraljud inom gastroenterologin. Läkartidningen. 17 Nov. 2009, No. 47.). Still, even when investigating submucosal tumours, the investigation may be started using a fibre-optic endoscope with a camera, and if the results are not satisfactory, the operator may switch to an endoscope with an ultrasound probe.

The edge of the outer tube is straight and, in the embodiments described above, not sharp. However, the edge may be made sharp, such that the outer tube has a cutting edge.

The material of the sheath is chosen such that the sheath may easily be inserted in the working channel of the endoscope in which it is to be supported, and such that the guide wire may be securely enclosed, yet freely movable inside the sheath. Examples of suitable materials are medical grade plastics materials, e.g., PTFE (polytetrafluoroethylene),FEP (fluorinated ethylene propylene) or polyolefin.

In the embodiments described above, the outer tube of the drill device is made of metal, e.g. medical grade steel. However, other materials, such as plastics may be used.

The inner cutting device is preferably made of metal, such as medical grade steel, in order to make it visible in an ultrasonogram. However, if the endoscope in which the endoscopic biopsy instrument is supported, uses another type of imaging device, such as a camera, other materials may be used.

The length of the endoscopic biopsy instrument, or rather the length of the guide wire, may be chosen depending on where in the body of the patient the biopsy sample is to be taken. For instance, for use in a gastroscope, the length of the guide wire may be approximately 160 cm.

Similarly, the length of the inner cutting device may be chosen depending on where the biopsy sample is to be taken. As non-limiting examples, a length of 5-7 mm may be sufficient for taking a superficial biopsy, whereas a biopsy of a submucosal tumour, such as GIST, may require a length of 10-12 mm, or even 15 mm.

In the embodiments described above, the inner cutting device has an inner core. The inner cutting device may also be constructed without an inner core, as long as the inner cutting device has a helical cutting edge and is stiff enough to penetrate into the tissue at the site of investigation.

In the embodiment shown in FIG. 6, there are two ways of manoeuvring the outer tube advancing device 223, i.e. by rotation of the second nut 226 or by depression of the end block 229. It may in many instances be advantageous to use rotation for advancing the outer tube 206, because experiments show that if depression of the end block 229 is used, the operator may have a tendency of slightly pulling back the instrument while depressing the end block 229. This may lead to shearing of the biopsy. Therefore, the instrument may very well be constructed without the end block 229. In such case, the guide bars 227 need not extend all the way through the actuator 211, but could be replaced by shorter guide bars or other guide elements guiding the sheath advancing portion 228. However, the end block 229 and the longer guide bars 227 may provide comfortable stability to the actuator 211.

In the method described above, when the sample has been cut out from the tissue, the outer tube is advanced on the inner cutting device, such that the sample is enclosed in the outer tube. Instead, the inner cutting device may be retracted into the outer tube. In other words, the inner cutting device and the outer tube should be moved in translation relative to each other in order to enclose the cut-out sample in the outer tube.

The endoscopic biopsy instrument is preferably a disposable instrument, for single use. However, it may be constructed for multiple use, as long as the materials chosen are suitable for the necessary sterilization, such as autoclaving.

The endoscopic biopsy instrument, the endoscope, and the method described above are particularly suitable for taking biopsy samples from submucous tumours. However, the invention may be used to advantage also for taking biopsy samples from other tumours and lesions.

The invention claimed is:

1. A method for taking a biopsy sample from a tissue of a subject, the method comprising:
   providing an endoscopic biopsy instrument comprising a guide wire arranged within a flexible sheath, wherein a drill device comprising an inner cutting device having a helical cutting edge is arranged at a first end of said guide wire, and an actuator for actuating said drill device, said actuator being arranged at a second end of said guide wire, wherein said drill device comprises an outer tube and said inner cutting device, said inner cutting device being slidable and rotatable inside said outer tube and comprising an inner core, said helical cutting edge being formed on a helical flange surrounding said inner core,
   inserting said first end of said guide wire into a body cavity of said subject by inserting the endoscopic biopsy instrument comprising said guide wire arranged within the flexible sheath in a working channel of an endoscopic insertion tube of an endoscope, wherein the endoscopic insertion tube is inserted into said body cavity and advanced until a distal end of the endoscopic insertion tube reaches a site to be investigated, wherein, during insertion, said inner cutting device is enclosed in said outer tube,
   advancing said guide wire arranged within the flexible sheath until said drill device comprising said outer tube and said inner cutting device is applied to a surface of said tissue from which said biopsy sample is to be taken,
   advancing said guide wire inside said flexible sheath such that said inner cutting device of said drill device is rotatingly bored into said tissue, such that said biopsy sample is cut out from said tissue, enclosing said biopsy sample in said outer tube by a translational movement of said outer tube in relation to said inner cutting device, wherein said guide wire is freely movable inside said flexible sheath, wherein said translational movement of said outer tube in relation to said inner cutting device is performed by the outer tube being advanced on the inner cutting device or by the inner cutting device being retracted into the outer tube, and retrieving said biopsy sample by withdrawing said first end of said guide wire from said body cavity.

2. The method for taking a biopsy sample from a tissue of a subject as claimed in claim 1, wherein said body cavity is part of gastrointestinal tract of the subject.

3. The method for taking a biopsy sample from a tissue of a subject as claimed in claim 1, wherein said outer tube is advanced over said inner cutting device on an outside of said inner cutting device.

4. The method for taking a biopsy sample from a tissue of a subject as claimed in claim 1, wherein the endoscope comprises an imaging device arranged in the endoscopic insertion tube, whereby the endoscopic biopsy instrument is securely guided to the site where the biopsy sample is to be taken.

5. The method for taking a biopsy sample from a tissue of a subject as claimed in claim 1, wherein said inner cutting device is made of metal.

6. The method for taking a biopsy sample from a tissue of a subject as claimed in claim 1, wherein said outer tube of said drill device has a cutting front edge.

7. The method for taking a biopsy sample from a tissue of a subject as claimed in claim 1, wherein said actuator comprises a plunger arranged to advance said outer tube of said drill device on an outside of said inner cutting device.

8. The method for taking a biopsy sample from a tissue of a subject as claimed in claim 1, wherein said actuator comprises a rotatable portion arranged to advance said outer tube of said drill device on an outside of said inner cutting device.

9. The method for taking a biopsy sample from a tissue of a subject as claimed in claim 1, wherein the endoscopic biopsy instrument is adapted to be inserted through a gastro scope.

10. The method for taking a biopsy sample from a tissue of a subject as claimed in claim 1, wherein the flexible sheath is made from a medical grade plastic material.

11. The method for taking a biopsy sample from a tissue of a subject as claimed in claim 10, wherein the medical grade plastic material is a medical grade plastic material selected from a list consisting of PTFE (polytetrafluoroethylene), FEP (fluorinated ethylene propylene), and polyolefin.

* * * * *